United States Patent [19]

Köcher et al.

[11] Patent Number: 5,547,860

[45] Date of Patent: Aug. 20, 1996

[54] SULPHOCOUMARIN-CONTAINING NUCLEOTIDES AND THEIR USE IN PROCESSES FOR DETECTING NUCLEIC ACIDS

[75] Inventors: Jürgen Köcher, Langenfeld; Wolfgang Springer, Wuppertal; Eberhard Kuckert, Leverkusen; Thomas Böcker, Leichlingen, all of Germany

[73] Assignee: Bayer Aktiengesellschaft, Leverkusen, Germany

[21] Appl. No.: 185,548

[22] Filed: Jan. 21, 1994

[30] Foreign Application Priority Data

Jan. 29, 1993 [DE] Germany ............... 43 02 459.9

[51] Int. Cl.$^6$ ............... C12P 19/34; C12Q 1/70; C12Q 1/68; C07H 21/04
[52] U.S. Cl. ............... 435/91.2; 435/5; 435/6; 435/91.1; 536/24.3; 536/24.33; 536/26.6
[58] Field of Search ............... 435/91.2, 91.1, 435/5, 6; 549/288; 536/26.6, 24.3, 24.33

[56] References Cited

U.S. PATENT DOCUMENTS

| 4,200,753 | 4/1980 | Henry et al. ............... 546/116 |
| 4,659,657 | 4/1987 | Harnish et al. ............... 435/21 |

FOREIGN PATENT DOCUMENTS

| 0063879 | 11/1982 | European Pat. Off. . |
| 0157384 | 10/1985 | European Pat. Off. . |
| 0200362 | 12/1986 | European Pat. Off. . |
| 0201184 | 12/1986 | European Pat. Off. . |
| 0320308 | 6/1989 | European Pat. Off. . |
| 0324474 | 7/1989 | European Pat. Off. . |
| 0329822 | 8/1989 | European Pat. Off. . |
| 90121348 | 6/1990 | European Pat. Off. . |
| 0427074 | 5/1991 | European Pat. Off. . |
| 0427073 | 5/1991 | European Pat. Off. . |
| 0513560 | 11/1992 | European Pat. Off. . |
| 0527433 | 2/1993 | European Pat. Off. . |
| 87/06270 | 10/1987 | WIPO . |
| 91/14697 | 10/1991 | WIPO . |

OTHER PUBLICATIONS

Proc. Natl. Acad. Sci. USA, vol. 78, No. 11, pp. 6633–6637 Nov. 1981, P. R. Langer et al.
F. W. Hobbs, J. Org. Chem., vol. 54, pp. 3420–3422, 1989.
C. Y. Lee et al., Arch. Biochem. Biphys., vol. 178, pp. 8–18 1977.
A. P. Feinberg and B. Vogelstein Analytical Biochemistry, vol. 132, pp. 6–13, 1983.
J. J. Dunn et al. J. Mol. Bio., vol. 113, pp. 237–251, 1977.
P. W. J. Rigby et al J. Mol. Biol., vol. 166, pp. 477–535, 1983.
IEEE Journal of Quantum Electronics, vol. 26, No. 12, 1990, pp. 2158–2161, Chekalin et al.
Folsom et al., Anal. Biochem 182:309–314, 1989.
EP 0527433 A1, Novel Fluorescent label, Dattasupta et al pp. 1–10, 17 Feb. 1993, filing date Jun. 8, 1992.

*Primary Examiner*—W. Gary Jones
*Assistant Examiner*—Dianne Rees
*Attorney, Agent, or Firm*—Sprung Horn Kramer & Woods

[57] ABSTRACT

The invention relates to the preparation, as substituents, of nucleotides possessing a fluorescent coumarin residue, the enzymic incorporation of these nucleotides into nucleic acids and the detection of nucleic acids of defined sequence by hybridization with a complementary, coumarin-labelled nucleic acid.

13 Claims, No Drawings

SULPHOCOUMARIN-CONTAINING NUCLEOTIDES AND THEIR USE IN PROCESSES FOR DETECTING NUCLEIC ACIDS

The present invention relates to the preparation, as substituents, of nucleotides possessing a fluorescent coumarin residue, the enzimatic incorporation of these nucleotides into nucleic acids and the detection nucleic acids of defined sequence by hybridization with a complementary, coumarin-labelled nucleic acid ( gene probe).

One of the most frequently used molecular-biological techniques for detecting homologous nucleic acid sequences is that DNA/DNA, RNA/RNA or RNA/DNA hybridization. In this technique, a nucleic acid (DNA or RNA), which is used as a probe, is labelled and brought into contact under hybridizing conditions with a nucleic acid (DNA or RNA) which is to be investigated. If homology exists between the nucleic acid which is used as a probe and the nucleic acid which is to be detected, the respective complementary nucleic acid single strands hybridize with the formation of a hybrid double strand. The hybrids are then detected.

In the past, the nucleic acids which were used as probes were, for the most part, labelled by the incorporation of radioactively derivatized ribonucleoside or deoxyribonucleoside triphosphates, and the hybrids were detected by autoradiography.

While this technique of labelling gene probes has proved to be a particularly sensitive method, it is also problematic owing to the handling of radioactive materials. Thus, special demands are made on laboratory safety and the disposal of radioactive compounds.

Furthermore, owing to their half-lives, radioactive materials can only be used for a limited period of time.

For this reason, some non-radioactive labelling procedures have already been developed in the past. In these cases, the gene probes are labelled with biotin molecules (EP 0 063 879) or digoxigenin molecules (EP 0 324 474 A1), for example, with incorporation of these detection molecules into a nucleic acid probe being effected by a chemical, photochemical or enzymic route. Following derivatization of the nucleic acid probe, hybridization takes place with the nucleic acid sequence which is to be detected. The hybrids are detected by binding a (strept)avidin-marker enzyme conjugate to biotin or by binding an anti-digoxigenin antibody-marker enzyme conjugate to digoxigenin.

Disadvantages of these methods are associated with the fact that the marker molecules bound to the nucleic acid probe are not detectable, and thus quantifiable, directly. Instead, these marker molecules, such as biotin or digoxigenin, must be detected by being bound to such molecules as enter into specific interactions with the marker molecules. These molecules, such as, for example, streptavidin for the detection of biotin, cannot, for their part, be detected directly, but must instead be provided in a suitable manner with a marker substance. This can, for example, be a fluorescent dye whose concentration can be determined by measuring the fluorescence. However, this marker substance is very frequently an enzyme which converts an added substrate into a form which can be evaluated quantitatively. Such a substrate can, for example, be the precursor of a dye, of a fluorescent dye or of a chemiluminescent compound.

It follows from this that further procedural steps are necessary in order to detect a hybrid using a labelled gene probe. Each additional procedural step carries with it the danger of errors or inaccuracies. The compounds which are required for binding to, for example, biotin or digoxigenin are biomolecules, such as streptavidin or antibodies, whose preparation is elaborate. These biomolecules have then to be coupled to additional marker enzymes. Many procedural steps are involved in the immunological and enzymic reactions and make evaluation of the hybridization reaction very complicated.

For this reason, substances are still required, for the hybridization of nucleic acid probes, which are readily available, which can easily be bound to nucleic acids and which can be detected in a straightforward manner.

The object of the invention was to develop labelling substances for nucleic acids which fulfil these pre-requisites.

It has been found that fluorescent nucleotides of the formula $$A—B—C \tag{I}$$

can be incorporated into nucleic acids by an enzymic route and provide intense and readily detectable labels, where A denotes a natural or synthetic nucleotide or a derivative thereof, B denotes a bridging member having two linkable centres, and C denotes a coumarin residue of the formula

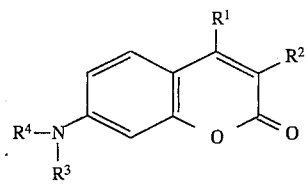

where $R^1$ is hydrogen or cyano, $R^2$ is phenyl or thiazolyl, which is bound in the 2, 4 or 5 position, where both residues carry a $SO_3H$ radical and can be further substituted, $R^3$ is H, $C_{1-4}$-alkyl, $C_{1-4}$-alkoxycarbonyl-$C_{1-4}$-alkyl, or phenylsulphonyl, where $C_{1-4}$-alkyl can be unsubstituted or substituted by hydroxyl, amino, carboxyl, $C_{1-4}$-alkoxycarbonyl or sulpho, and where phenylsulphonyl can be unsubstituted or substituted once or more than once by chlorine, bromine, $C_{1-4}$-alkyl or sulpho.

$R^2$ or $R^3$ can be substituted by a primary or secondary amino group, hydroxyl, carboxyl or $C_{1-4}$-alkoxy carbonyl or itself represent such a substituent, or $R^2$ or $R^3$ can be converted by hydrolysis into such a group;

for the case that $R^4$ is a substituent and not a bond, the bonding of C to B is effected by way of a further substituent on the residue $R^2$, such as, for example, amino or carboxyl.

Compounds of the formula (I) are preferred where

A represents a residue which is selected from the group of natural or synthetic nucleotides consisting of AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-MeCDP, 5-Me-CTP, 5-MeO-CMP, 5-MeO-CDP, 5-Me0-CTP, and deoxynucleotides or dideoxynucleotides from this series, as well as further derivatives thereof, is a bifunctional bridging member having a chain length of up to 50 atoms, where the atoms can be C, H, O, N or S. This bridging member can be linear or branched, and C represents a coumarin residue of the formula

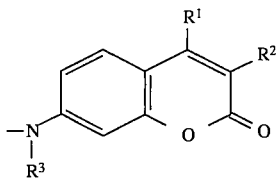

in which
R¹ possesses the abovementioned meanings,
R² is phenyl or thiazolyl, bound in the 2, 4 or 5 position, where phenyl is substituted by a sulpho group and is additionally substituted by carboxyl, $C_{1-4}$-alkylcarbonyloxy, amino, $-NH-C_{1-4}$-alkyl,$-(CH_2)_{1-4}-NH_2$, $C_{1-4}$-alkyl, cyano, fluorine, chlorine, bromine or sulpho and where the thiazolyl residue is substituted by a sulpho group and can optionally carry additional substituents,
or where the thiazolyl residue is condensed in the 4 and 5 positions with a benzene ring which is substituted by a sulpho group and can be additionally substituted,
and
R³ is hydrogen, methyl, ethyl, $-(CH_2)_{1-4}-OH$, $-(CH_2)_{1-4}-NH_2$ or $-(CH_2)_{1-4}-COOH$ or $(CH_2)_{1-4}-SO_3H$.

Compounds of the formula (I) are very particularly preferred where
A has the abovementioned meanings,
B is a bifunctional bridging member having 2 to 20 atoms selected from the group comprising C, H, O, N and S.

Such bridging members can be peptide derivatives, hydrocarbons, such as alkylene, alkenylene, alkenylene, arylene or substituted derivatives thereof, polyalcohols, polyalkoxides, polyethers, polyamines, polyimines, carbohydrates, $-CH=CH-CH_2NH-$, -glycyl- glycyl-glycyl-, $-NH(CH_2)_5CO-$, spermine or spermidine, $-NH-(CH_2)_6-NH-$, $-NH-CH_2CH_2-NH-$, $-CH=CH-CH_2-NH-CO-(CH_2)_5-NH-CO-$ or $-CH=CH-CH_2-NH-CO-(CH_2)_5-NH-CO-(CH_2)_3-$
and
C is a coumarin residue having the above-mentioned formula, where
R¹ has the abovementioned meaning,
R² is a phenyl or thiazolyl, bound in the 2 position,
where phenyl is substituted by sulpho and is additionally substituted by para-carboxyl, para-amino, para$-NH-C_{1-4}$-alkyl, para$-CH_2-NH_2$, cyano, methyl or ethyl, and where thiazolyl is substituted by sulpho and is additionally substituted by chloro, cyano or carboxyl, or the thiazolyl residue is condensed in the 4 and 5 positions with a benzene ring which is substituted by sulpho and can additionally contain carboxyl or amino as substituent,
and
R³ has the abovementioned meanings.

The use of coumarins as fluorescent dyes is advantageous as compared with the use of fluorescein, for example, because coumarins are distinguished by a particularly high degree of stability and fastness to light.

The substances according to the invention are as a rule prepared by linking together a coumarin dye component and a nucleotide component. Both components contain reactive centres which can be derivatized chemically and which can be linked to each other. Such centres are frequently located in side chains of the two components. Once the two components have been linked via these reactive centres in the side chains, the compounds according to the invention are obtained and the linked side chains of the nucleotide moiety and the coumarin moiety form the bridging member B of the formula (I).

Hydroxyl, amino or carboxyl groups, for example, can be used as reactive and derivatizable centres. By using methanesulphonyl chloride, N,N'-carbonyldiimidazole or N-hydroxysuccinimide, for example, hydroxyl and carboxyl groups can be converted to form reactive esters which can be linked to O-nucleophiles or N-nucleophiles with the formation of carboxylic acid esters or carboxamides.

Nucleotides modified by a reactive side chain can be made available by processes described in the literature; see, for example, D. Bergstrom et al., Synlett 1992, 179. Those compounds which are described in particular detail are derivatives of uridine 5'-triphosphate and deoxyuridine 5'-triphosphate having an allylamine side chain in the 5 position (P. R. Langer et al., Proc. Natl. Acad. Sci. USA, 78, 6633 (1981) or having a propargylamine side chain (F. W. Hobbs, J. Org. Chem. 54, 3420 (1989)), as well as adenosine 5-triphosphate derivatives having hexamethylenediamine side chains in the 6 and 8 positions [V. Folsom et al., Anal. Biochem. 182, 309 (1989); C.-Y. Lee et al., Arch. Biochem. Biophys. 178, 8 (1977)].

Some of these compounds have by now also become commercially available. Coumarin dyes are likewise known from the literature, for example from EP 90 12 1348. These products can be obtained with side chains and reactive centres located upon them, which centres can be linked to the side chain of a modified nucleotide. Thus, a coumarin dye having a carboxyl substituent can be converted into a reactive carboxylic acid ester, for example using N-hydroxysuccinimide, which then reacts with an amino group of one of the abovementioned modified nucleotides to form the carboxamide.

A problem associated with these linking reactions is the difference in solubility of the nucleotide and coumarin components. Nucleotides are almost exclusively soluble in water whereas coumarins are normally either insoluble or only very sparingly soluble in $H_2O$. Coumarins are likewise only very poorly soluble in many organic solvents. In the case of two compounds which differ to such a degree in their solubility, the linking reaction described above can only be effected with difficulty. Solvent mixtures (water and organic solvent) are required whose mixing ratio must be determined accurately in order to keep both reactants in solution in adequate quantity and thus to obtain a satisfactory yield of reaction product.

The coumarin-substituted nucleotides of the formula (I) according to the invention contain a coumarin dye having at least one sulphonic acid group. The nucleotide and coumarin components can therefore be linked in aqueous solution because the sulphonic acid groups make the coumarin molecules adequately soluble in water. In this way, the products of the formula (I) according to the invention can be obtained much more simply than comparable products without sulphonic acid groups. Sulphonated coumarins can be synthesized by using, during the synthesis, suitable precursors which are substituted by sulpho groups.

However, sulphonated coumarins are preferably prepared by subsequently derivatizing coumarins, after their synthesis, by means of suitable sulphonating processes. Reagents which are suitable for use as sulphonating agents are concentrated sulphuric acid having a sulphuric acid content of 70% or more, 100% sulphuric acid, chlorosulphonic acid and oleum having concentrations of up to 65%.

The coumarins are converted into the sulphonated derivatives by introducing the dyes into one of the abovementioned sulphonating reagents, preferably at 0° C. to 50° C., and stirring, likewise preferably at 0° C. to 50° C., until the starting material has completely reacted. The product can be isolated and purified by known methods.

This invention further relates to the use of the nucleotides of the formula (I) which have been substituted by sulphocoumarins for detecting nucleic acids of defined sequence. For this purpose, nucleic acids are derivatized by the enzymic incorporation of the nucleotides which have been substituted by coumarins. The resulting fluorescent nucleic acids can be used as gene probes for detecting homologous nucleic acid sequences by hybridization. The fluorescent hybrids which form can be detected without difficulty.

A further option for using the fluorescent nucleotides of the formula (I) according to the invention arises from the possibility of incorporating these molecules into nucleic acids during enzymic amplification processes. The nucleic acid fragments which arise as a result of specifically amplifying the nucleic acid to be analysed in the presence of the fluorescent nucleotides according to the invention also contain these fluorescent nucleotides of the formula (I) in place of natural nucleotides. In this way, the nucleic acid fragments prepared by amplification become fluorescent, so that their formation can be detected simply and directly. The resulting fluorescent nucleic acid fragments may also be employed as labelled gene probes for hybridization experiments.

Nucleic acids (DNA and RNA) can be derivatized with fluorescent nucleotides by various enzymic methods. The "random-primed" method (Anal. Biochem. 132, 6 (1983)) is a method for derivatizing DNA and is based on the hybridization of a mixture of all possible hexanucleotide sequences with the DNA to be modified. Starting from the 3'-OH ends of these hexanucleotides, the strand complementary to the single strand is synthesized using DNA polymerases such as the Klenow enzyme, or other DNA polymerases. Four deoxyribonucleotides, offered as substrates for the DNA polymerases, are incorporated into the complementary strand. If at least one of these deoxyribonucleotides is replaced by a coumarin-substituted nucleotide, complementary DNA is obtained which is labelled with fluorescent dyes.

Instead of a mixture of short oligodeoxyribonucleotides possessing the widest possible variety of sequences, oligodeoxyribonucleotides having specific sequences ("specific primers") can also be used. These "specific primers" bind in a uniform manner only to the complementary segment of a single-stranded DNA and synthesis of the complementary DNA only begins from the 3'-OH end of these specific primers. As in the case of the "randomprimed" method, labelling of the complementary DNA is brought about in this case as well by offering the DNA polymerases at least one nucleotide which contains a coumarin dye.

The method of "nick translation" (J.Mol.Biol. 113, 237 (1977)) is based on the action of a small quantity of the enzyme DNase I on double-stranded DNA. The DNase I produces single-stranded breaks in the double-stranded DNA. At the same time, E. coli DNA polymerase I and the 4 deoxyribonucleotides serving as substrate for this enzyme are present in the reaction mixture. The E. coli DNA polymerase I splits off the 5'-terminal deoxyribonucleoside at the single-stranded breaks and at the same time incorporates one of the deoxyribonucleotides offered as substrate onto the adjacent free 3'-OH end. By repetition of this process, the single-stranded break migrates to the 3' end. If at least one of the four nucleotides offered as substrate is replaced by a coumarin-substituted nucleotide, fluorescent DNA is obtained using this "nick translation method". For 3' end-labelling of double-stranded or singlestranded DNA, use is made of the enzyme terminal transferase which links deoxyribonucleotides or ribonucleotides onto the 3'-OH end. This enzyme requires at least one type of deoxyribonucleotide or ribonucleotide as substrate. Instead of a natural nucleotide, deoxyribonucleotides or ribonucleotides which are substituted by coumarins can also be employed as enzyme substrates. The nucleic acid, which has been extended at the 3'-OH end, then contains these compounds and as a consequence becomes fluorescent.

The method of "reverse transcription" converts singlestranded ribonucleic acid, or double-stranded ribonucleic acid following conversion into the single strands, into the corresponding DNA. For this purpose, oligodeoxyribonucleotides are annealed, as primers, onto the complementary sections of the RNA. Using the enzyme reverse transcriptase, the DNA strand which is complementary to the RNA strand is synthesized starting from the 3'-OH end of the primer. In this DNA synthesis, four types of deoxyribonucleotides are offered as enzyme substrates, at least one being a coumarin-substituted derivative. Reverse transcriptase also incorporates this material into the newly formed DNA strand, as a result of which the latter is labelled with fluorescent dyes.

A further option for preparing nucleic acids containing the coumarin-substituted nucleotides according to the invention arises from the use of enzymes which prepare RNA from a DNA template. Such enzymes are phage-encoded RNA polymerases, such as SP6, T3 or T7 RNA polymerases. These enzymes require double-stranded DNA which contains the SP6, T3 or T7 promoters, as well as four ribonucleotides as substrates for the RNA synthesis (J. Mol. Biol. 166, 477 (1983)).

The promoter regions can be inserted, for example, into transcription vectors; another possibility is the use of short, single-stranded nucleic acids which are constructed in such a way that, as a result of the formation of hairpins, they contain the double-stranded promoter regions which are required by the RNA polymerases (EP 427 073 and EP 427 074). RNA molecules having a fluorescent label are obtained by using as substrates ribonucleotides which are substituted by coumarin dyes.

The fluorescent nucleic acids prepared by these methods may be used as gene probes for detecting nucleic acids of defined sequence by hybridization. The gene probes which are labelled with fluorescent dyes may be used in all known hybridization assays. Such methods are well known from the literature by way of numerous publications. The fluorescent hybrids can be detected directly by fluorescence spectroscopy or fluorescence microscopy.

This process according to the invention can be applied particularly advantageously for insitu hybridization using fixed whole cells, fixed tissue smears or isolated chromosomes, as well as for the detection of viral and bacterial infections in blood, serum or other body fluids.

This invention further relates to the use of the coumarin-substituted nucleotides according to the invention as enzyme substrates during an amplification process. Both DNA and RNA amplification techniques may be employed.

The most familiar amplification process is known under the name of "polymerase chain reaction (PCR)" (EP 200 362). In this process, the nucleic acid which is to be detected in a biological sample is converted into single strands and hybridized with two oligonucleotides (primers). The two oligonucleotides are complementary to different constituent regions of the nucleic acid double strand to be detected, one oligonucleotide in each case hybridizing to one of the two separated single strands. Following hybridization, treatment takes place with polymerases, preferably with Taq DNA polymerase, and with deoxyribonucleotides as the enzyme substrate. Once the complementary DNA has been synthesized, starting from the 3'-OH ends of the primers, all the nucleic acid double strands are once again converted into single strands and the process, consisting of hybridizing the primers to the nucleic acid and subsequently polymerizing, is repeated. By repeating this procedure a number of times, the DNA which is contained in the sample and which is to be detected can be amplified up to $10^9$ times.

By using at least one deoxyribonucleotide containing a coumarin substituent during the polymerization process, amplified nucleic acid possessing a fluorescent label is obtained. This fluorescence can be enlisted for detecting the nucleic acids. This can take place after appropriate isolation of the fluorescent DNA, for example by precipitating this DNA with EtOH. Furthermore, this working up can be effected by isolating the fluorescent DNA on complementary DNA, preferably on that DNA which is immobilized on solid phases.

Other methods of amplifying DNA or RNA which permit the use of the coumarin-substituted nucleotides according to the invention and which lead to the preparation of fluorescent amplification products are, for example, the LCR (EP 320 308), the NASBA (EP 329 822), the Qβ(PCT 87/06270) or the HAS (EP 427 074) techniques.

The following examples illustrate the described invention but are in no way to be understood as restricting this invention.

EXAMPLES

Example 1

4.0 g of the dye 7-(N-ethyl-N-carboxy-trimethylene-amino)-3-(4',5'-benzo-thiazo-2'-yl)coumarin are introduced slowly into 40 ml of oleum (20%) and the mixture is stirred at room temperature for 2 h. It is then added to 100 g of ice and adjusted to pH 7 with conc. sodium hydroxide solution. The water is to a large extent distilled of on a rotary evaporator and the residue is heated under reflux for 3 h together with 400 ml of 10% hydrochloric acid. Following neutralization with conc. sodium hydroxide solution, the mixture is once again evaporated to dryness and the solid residue is stirred with 500 ml of DMF. The mixture is filtered to remove insoluble salts and the DMF is removed on a rotary evaporator. Following stirring for extraction with 10 to 20 ml of diethyl ether, 2.2 g (47%) are obtained of the product of the formula

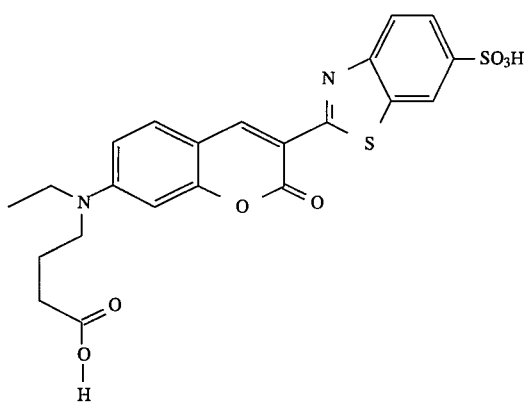

(Na salt of the sulphonic acid according to MS-FAB; the substance crystallizes with one mole of DMF) m.p.:>250° C.

Example 2

In an analogous manner, the product of the formula

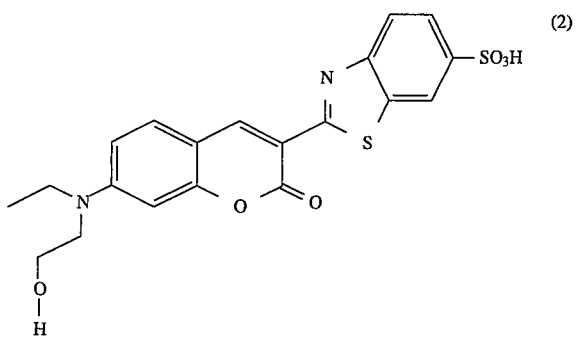

is obtained in 50% yield from 7-(N-ethyl-N-β-hydroxy-ethylamino)-3-(4',5'-benzothiazol-2'-Yl)coumarin m.p.: 270° C. (Na salt)

Example 3

Preparation of

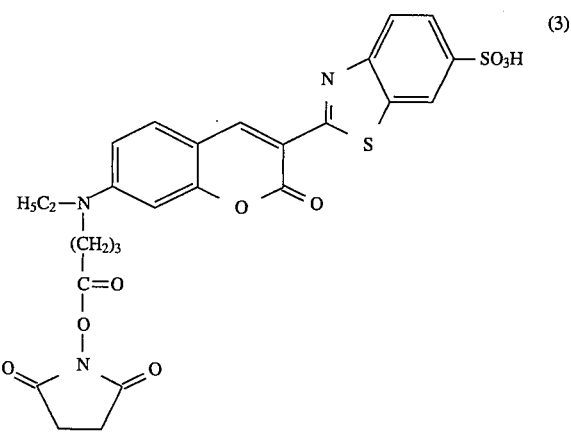

3.0 g (6.1 mmol) of the compound (1) of the formula

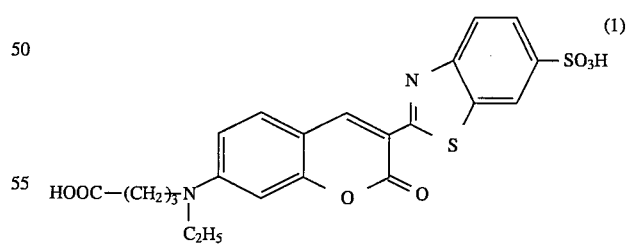

are dissolved in 90 ml of dimethylformamide. The solution is heated to 50° C. 1.5 ml of pyridine (1.47 g, 18.5 mmol) and 5.7 g of disuccinimidyl carbonate (22.1 mmol) are added at this temperature. After stirring at 50°to 60° C. for 3 h, conversion to the N-hydroxysuccinimide ester is complete. After removing the dimethylformamide by distilling off in vacuo, the remaining residue is purified by column chromatography (silica gel, eluent toluene/ ethanol 1:2). 1.8 g are obtained of a yellow solid (50%) of the formula (3).

Example 4

Preparation of

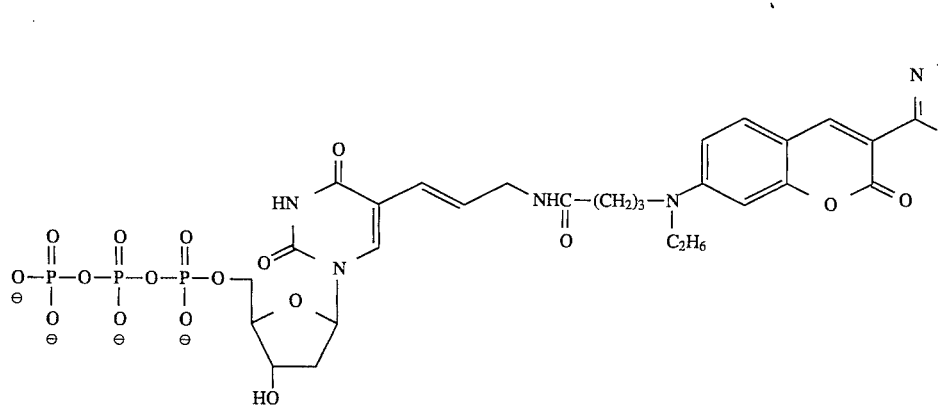

Na₄ salt 9 mg of 5-allylamino-dUTP (Sigma, $1.6 \times 10^{-5}$ mol) are dissolved in 5 ml of H₂O. The solution is adjusted with 0.2 molar Na₂CO₃ to pH 9.5 and 22 mg of the activated carboxylic acid ester of the formula (3) ($3.8 \times 10^{-5}$ mol) are then added in solid form. During the reaction at room temperature, the pH is maintained at between 8.5 and 9.5 by adding 0.2 molar Na₂CO₃. After stirring at room temperature overnight, a further 20 mg ($3.4 \times 10^{-5}$ mol) of the dye of the formula (3) are added within the space of 2 h and stirring is continued at room temperature. After a total running time of 45 h, 5-allylamino-dUTP can no longer be detected by thin layer chromatography (silica gel, ethanol/H₂O 5:2). The reaction mixture is evaporated to dryness in vacuo. The resulting reaction product is purified by being chromatographed three times on Sephadex G 10 (eluent H₂O). 3.8 mg are obtained of the coumarinsubstituted deoxyribonucleotide of the formula (4).

Example 5

Preparation of

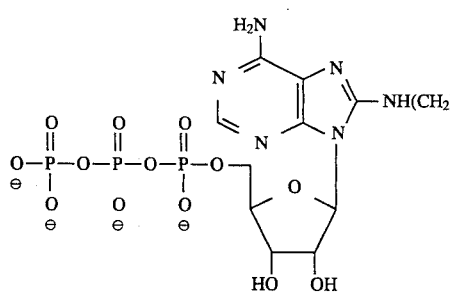

Na₄ salt 14 mg of 8-(6-aminohexyl)amino-ATP (Sigma, $2.26 \times 10^{-5}$ mol) are dissolved in 10 ml of H₂O. The resulting solution is adjusted to pH 9.5 with 0.1 molar Na₂CO₃. 32 mg of the coumarin derivative of the formula (3) ($5.5 \times 10^{-5}$ mol) are then added at room temperature and the mixture is stirred at room temperature for 20 h. The pH is maintained within the range from 8.5 to 9.5 by adding 0.1 molar Na₂CO₃. After the reaction is complete, 8-(6-aminohexyl)amino-ATP can no longer be detected by thin layer chromatography (silica gel, EtOH/H₂O 5:2). The reaction mixture is evaporated to dryness in vacuo.

The resulting reaction product is purified by being chromatographed three times on Sephadex G 10 (eluent H₂O). To avoid contamination with RNAses, all the equipment used for the chromatography is sterilized before use. 8.9 mg are obtained of the fluorescent nucleotide of the formula (5).

EXAMPLE 6

Preparation of

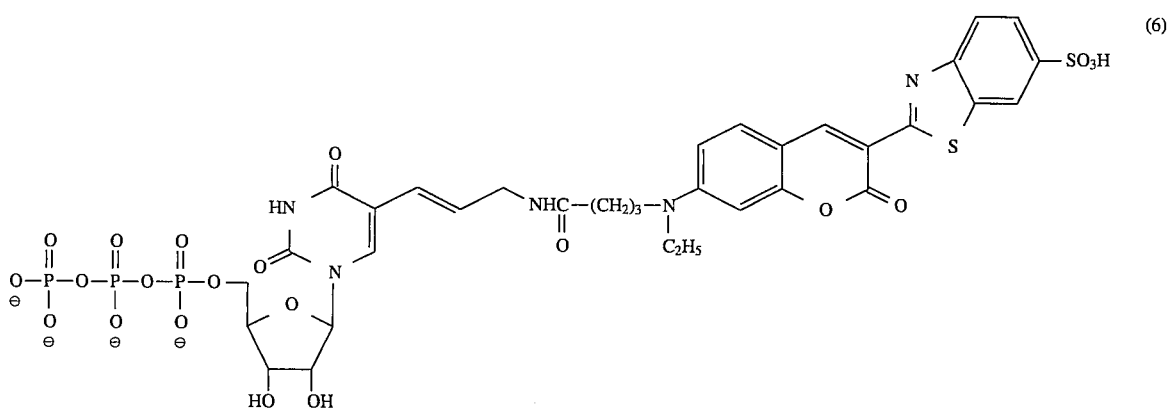

Na₄ salt 10 mg of 5-allylamino-UTP ($1.6 \times 10^{-5}$ mol) are dissolved in 5 ml of H₂O. The pH is adjusted to pH 9.5 by adding 0.2 molar Na₂CO₃ solution, and 20 mg ($3.4 \times 10^{-5}$ mol) of the coumarin of the formula (3) are added at room temperature. The mixture is stirred at room temperature for 8 h, with the pH being maintained at a value of 8.5 to 9.5 by adding 0.2 molar Na₂CO₃ solution. The reaction mixture is evaporated to dryness in vacuo. The resulting reaction product is purified by being chromatographed three times on Sephadex G 10 (eluent H₂O). To avoid contamination with RNAses, all the equipment used for the chromatography is sterilized before use. 5.5 mg are obtained of the fluorescent nucleotide of the formula (6).

product (7), together with a small amount of remaining starting material (3), can be detected by thin layer chromatography (silica gel, toluene/ethanol 1:5). The reaction mixture is concentrated to dryness in vacuo and then fractionated by column chromatography (silica gel, toluene/ethanol, 1:5, and then ethanol/H₂O, 150:1).

The product-containing fractions are concentrated to dryness in vacuo and the residual product is stirred for extraction with 50–100 ml of diethyl ether. 398 mg (39%) are obtained of the substance of the structure (7) (m.p. 250° C.).

Example 7

Preparation of

Example 8

Preparation of

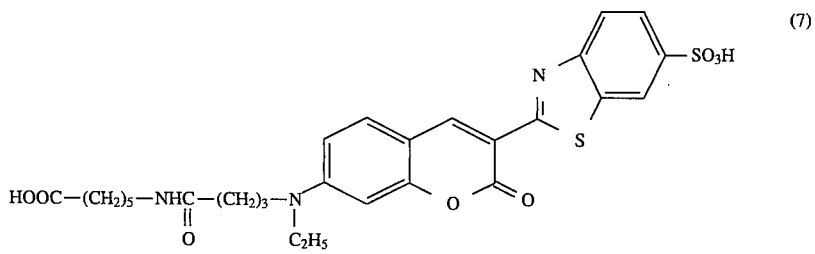

200 mg of 6-aminocaproic acid ($1.5 \times 10^{-3}$ mol) are dissolved in 5 ml of water. The pH of the solution is adjusted to 9.5 with 0.1 molar Na₂CO₃ solution. 1.0 g of the carboxylic acid ester of the formula (3) ($1.7 \times 10^{-3}$ mol) is added at room temperature and stirring then continued at room temperature. The pH is maintained at a value of 9 to 9.5 by adding 0.1 molar Na₂CO₃ solution. After stirring for 20 h, the new

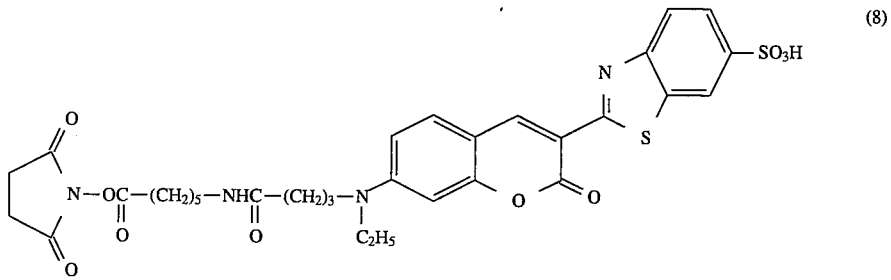

0.35 g of compound (7) ($5.8 \times 10^{-4}$ mol) and 0.46 g of N,N'-disuccinimidyl carbonate ($1.8 \times 10^{-3}$ mol) are dissolved in 3.5 ml of DMF. The reaction mixture is heated at 50° to 60° C. for 3 h. The solution is concentrated to dryness in vacuo and the resulting product (8) is isolated by column chromatography (silica gel, toluene/ ethanol 1:2). The product-containing fractions are concentrated to dryness in vacuo and the resulting product is stirred for extraction with 50 ml of diethyl ether. 248 mg (61%) are obtained of compound (8) [m.p. 80° C. (decomp.)].

Example 9

When 5-allylamino-dUTP is reacted with compound (8) and the subsequent procedure is as described in Example 4 for the reaction with compound (3), the fluorescent nucleotide (9) is obtained of the formula Example 10

When 8-( 6-aminohexyl ) amino-ATP is reacted with compound (8) and the subsequent procedure is as described in Example 5 for the reaction with compound (3), the fluorescent nucleotide (10) is obtained of the formula Example 11

When 5-allylamino-UTP is reacted with compound (8) and the subsequent procedure is as described in Example 6 for the reaction with compound (3), the fluorescent nucleotide (11) is obtained of the formula

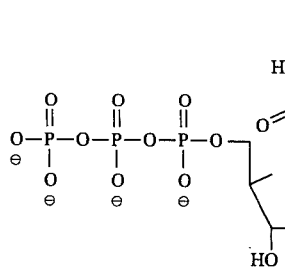
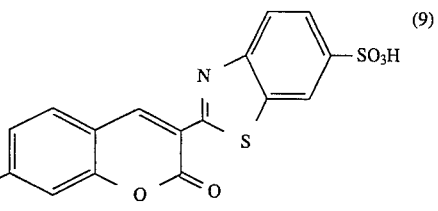

(9)

Na$_4$ salt

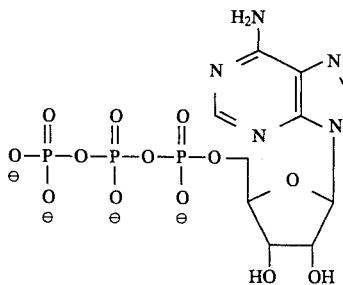
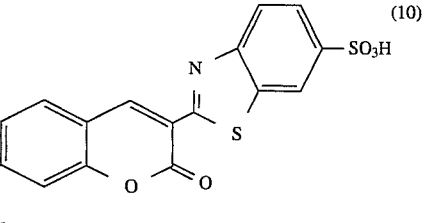

(10)

Na$_4$ salt

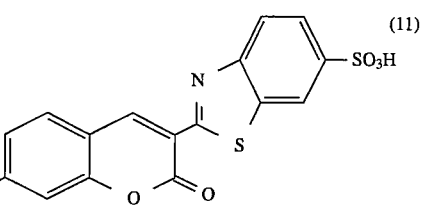
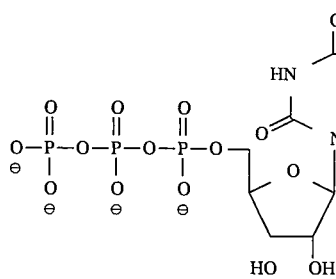

Na₄ salt

Example 12

Fluorescent nucleotides which can be employed for the enzymic labelling of nucleic acids in exactly the same way as compounds (4) to (11) are obtained in an analogous manner by linking the amino-substituted nucleotides to compound (2) using suitable auxiliary reagents such as N,N'-carbonyldiimidazole.

Example 13

3' end-labelling of polynucleotides using fluorescent nucleotides.

A 1.7 kb long polynucleotide probe was labelled at the 3' end with the coumarin-dUTP of the formula (4), with fluorescein-dUTP, with hydroxy-coumarin-dUTP and resorufin-dUTP using an end-labelling kit from Boehringer Mannheim. Approximately 50% 3' end-labelling is achieved after 60 minutes at 37° C. in a 50 μl mixture containing 10 μl of reaction buffer (potassium cacodylate, 1 mol/l; Tris/HCl, 125 mmol/l; bovine serum albumin, 1.25 mg/ml; pH 6.6; 25° C.), 1–2 μg of oligonucleotide, 25 units of terminal transferase, $CoCl_2$, 2.5 mmol/l, and 0.025 mmol of fluorescent dUTP.

The labelled polynucleotides were separated from the free NTP's by suitable precipitation methods or columnchromatographic methods and employed as gene probes in slot-blot hybridizations or liquid hybridizations (Examples 18 and 19).

The fluorescence of the labelled DNA was measured in a fluorescence photometer at the excitation and emission wavelengths corresponding to the particular coumarin dye. It was observed that the fluorescence of the DNA labelled with the coumarin-dUTP of the formula (4) was higher by a factor of 100 than that of the DNA which had been labelled using fluorescein, hydroxycoumarin or resorufin.

Example 14

Fluorescence-labelling of DNA by random-primed labelling using Klenow enzyme

The method of random-primed DNA labelling is based on the hybridization to the DNA which is to be labelled of a mixture of hexanucleotides of all the possible base sequences. The complementary strand is subsequently synthesized from the 3' ends of the random primers using Klenow enzyme. In this process, the modified deoxyribonucleoside triphosphates, which are offered as substrate and which, as in this example, are labelled with coumarin dyes, are incorporated into the newly synthesized complementary strand. Virtually all the sequence combinations are present in the hexanucleotide mixture serving as primer, so that these hexanucleotides bind to the DNA employed on the basis of statistical distribution and thus guarantee labelling of the total DNA in equal proportions. The reaction is independent of the length of the DNA. 200 bp long fragments can be employed just as well as can polynucleotides having a length of 5 kb.

The compound of the formula (4) is very well incorporated into the DNA and, in comparison to fluorescein-dUTP, yields fluorescence signals which are up to 100 times greater.

DNA having a particularly high degree of specific labelling is obtained when the random-primed DNA labelling method is used. The smallest quantities can, therefore, be labelled. DNA labelled in this manner can be used in a wide variety of hybridization techniques, such as, for example, those described in Examples 18 and 19.

Example 15

Fluorescence-labelling of DNA by PCR amplification

The polymerase chain reaction (PCR) is described in patents EP 200 362 and EP 201 184. This thermocyclic amplification process is based on the amplification of DNA fragments of defined size by using starter oligonucleotides which, with the aid of a thermostable Taq polymerase, synthesize sequence regions, which are in each case given by the sequence of the starter oligonucleotide, from the 5' end in a complementary manner to the starting strand. By denaturing the double strand, annealing the starter oligonucleotides (primers) and extending new DNA strands with the aid of the Taq polymerase, a million-fold multiplication of the starting DNA fragment is achieved by multiple repetition of these cycles.

During the amplification, fluorescent NTP's can also be inserted in addition to the free nucleoside triphosphates and in this way many fluorescent molecules can be incorporated into the amplified DNA. The fluorescence-labelled DNA can then be introduced directly into hybridization experiments and in this way highly sensitive gene probe tests can be carried out.

The following were included in the PCR reaction: 2 μg of genomic DNA from Nitrosomonas europeae, 2 μmol of primer 1 (5'dATCCAGTTGCTTCAAC) (seq ID No: 1) and primer 2 (5'dACTGGCAGGCAGCAG), (seq ID No: 2) 2.5 units of Taq polymerase from Cetus/Perkin-Elmer and 200 μmol of each dNTP in a total of 100 μl of PCR buffer (50 mM KCl, 10 mM Tris/HCl, pH 8.3, 1.5 mM $MgCl_2$ and 0.01% gelatin). In each case, 40 μl of the fluorescent dUTP of the formula (4) as fluorescent nucleotide supplemented by 160μl of dTTP were employed. The amplification was carried out in a Cetus/Perkin-Elmer PCR processor.

Using the samples, an initial melting of the DNA was first carried out at 94° C. for 2 minutes 30 seconds, and then, in each cycle, the DNA was denatured at 94° C. for 1 minute, primer annealing was carried out at 40 to 45° C. for 2 minutes, and primer extension was carried out at 72° C. for 3 minutes. After 35 cycles, a final 20-minute extension was carried out at 72° C. and the samples were then cooled at 4° C. The amplified DNA labelled with compound (4) gives fluorescence signals which are up to 100 times stronger than those given by amplified DNA labelled with fluorescein-dUTP.

Example 16

RNA labelling by in-vitro transcription using fluorescent ribonucleotides and RNA polymerase Linearized template DNA containing a T7 or T3 promoter is transcribed into RNA in vitro by RNA polymerases using ATP, GTP, CTP and UTP, and corresponding fluorescent NTP's. The RNA labelled in this way may be employed in hybridization and RNA-amplification tests as well as in in-situ hybridization. Evaluation takes place directly by measuring the fluorescence of the labelled RNA.

A pSK Bluescript construct, containing a T7 promoter and a 1.7 kb DNA insert, was employed for the RNA transcription and fluorescence measurement. A transcription mixture having the following composition was made up:

10 μl of linearized DNA construct (0.5 μg)

4 μl of transcription buffer (40 mM Tris/HCl pH 7.9; 6 mM $MgCl_2$; 10 mM NaCl, 2 mM spermidine), 2 μl of 100 mM dithioerythritol 1 μl of 10 mM ATP 1 μl of 10 mM CTP 1 μl of 10 mM GTP 1 μl of 10 mM UTP 0.5 μl of T 7 polymerase (10 units)

In order to label the RNA with fluorescent nucleotides, 10 mM of the compound of the formula (5) was employed instead of UTP.

The mixture is incubated at 37° C. for 2 hours; an ethanol precipitation is subsequently carried out and the precipitate is washed five times with ethanol, and the RNA is then redissolved in TE buffer. The fluorescence was determined in a fluorescence photometer.

Examle 17

Fluorescence labelling of RNA by means of T7/T3 hairpin amplification

Hairpin amplification is a method of amplifying RNA which is described in patent EP 427 074. If a hairpin oligonucleotide is used which forms a T7 or T3 promoter for transcribing RNA with the corresponding RNA polymerase, the option exists of using fluorescent NTP's to label the RNA and amplify it a millionfold. By using a fluorescence label, direct evaluation of the amplification is possible in a photometer by way of the fluorescence signal, and no elaborate ELISA processes become necessary.

The transcription mixture was made up as indicated in Example 16. The compound of the formula (6) was employed as the fluorescent nucleotide. The fluorescence of the labelled oligonucleotide transcripts was evaluated by polyacrylamide gel electrophoresis.

Example 18

Slot-blot hybridization using fluorescence-labelled DNA or RNA oligonucleotide or polynucleotide probes Hybridization was carried out in accordance with customary processes at an incubation temperature of 40° to 68° C. Different substances were added, in each case depending on the hybridization temperature which was used. Dextran sulphate or other polymers were employed in order to increase the rapidity and the degree of the hybridization. Detergents and blocking reagents, such as dried milk, Denhardt's solution, heparin or SDS, were added in order to suppress non-specific binding of the DNA to the membrane. Denaturing agents, such as urea or formamide, may be employed in order to reduce the melting temperature of the hybrids, thus permitting lower hybridization temperatures to be employed. Apart from this, non-specific binding of gene probes to non-homologous DNA on the blot can be reduced by adding heterologous DNA.

To prepare for the hybridization, 50 to 500 ng of unlabelled genomic DNA from Nitrosomonas europeae were first denatured at 100° C. for 5 minutes and then cooled to 0° C.; the DNA was then transferred to pretreated nitrocellulose or nylon membranes with the aid of a MinifoldII filtration apparatus from Schleicher and Schell and fixed at 80° C. for 2 hours.

The filters were hybridized at 68° C. for at least 1 hour in a sealed plastic film bag or plastic box containing at least 20 ml of hybridization solution per 100 $cm^2$ of filter.

The solution was replaced by 2.5 ml/100 $cm^2$ of filter of hybridization solution to which 100 ng of fluorescent gene probe had been added. The filters were incubated with gentle shaking at 68° C. for at least 6 hours.

The filters were then washed twice at room temperature for 5 minutes on each occasion with at least 50 ml of 2× SSC, 0.1% SDS per 100 $cm^2$ of filter and then twice at 68° C. for 15 minutes on each occasion with 0.1× SSC, 0.1% SDS.

The filters were then used directly for detecting the hybridized DNA.

Solutions:

20× SSC: 3M NaCl, 1, 0.3M Na citrate, pH 7.0

Hybridization solution: 5× SSC; 0.1% N-lauroylsarcosine, Na salt, 0.02% SDS; 0.5% blocking reagent (Boehringer) solution to be made up at 50 to 70° C.

Other hybridization solutions which likewise can be employed for slot-blot hybridization are, for example:

Hybridization mix 2: 50% formamide; 7× SSC; 2× Denhardt's solution (100× Denhardt's : 2% Ficoll, 2% polyvinylpyrrolidone, 2% bovine serum albumin); 300 μg/ml calf thymus DNA Hybridization mix 3: 6× SSC; 10× Denhardt's solution; 50 μg of herring sperm DNA; bovine serum albumin, 0.1%

Hybridization mix 4: 5× SSC; 5% PEG; 5% dried milk powder; 0.01M sodium pyrophosphate.

Readout was effected by way of the fluorescent coumarin dye bound in the sample. The fluorescent slot blots on the filter were evaluated quantitatively in a Shimadzu CS 930 scanner.

Example 19

Liquid hybridization using the fluorescence-labelled oligonucleotide or polynucleotide probes Liquid hybridizations were carried out as sandwich hybridizations using streptavidin-coated magnetic particles from Dynal for separating the hybridization complex.

The liquid hybridization tests were carried out as sandwich tests using 100 ng of 5'-biotinylated capture oligonucleotide probe of the nucleotide sequence 5'dCTGCTCGTAGACAATGCGT (seq ID No.: 3,) 100 ng of fluorescence-labelled oligonucleotide probe (detector gene probe) of the nucleotide sequence 5'dATCCAGTTGTGTCTTAAC (seq ID No.: 4) and different concentrations (50 ng to 1000 ng) of Nitrosomonas target DNA in a volume of 50 µl.

After heating at 100° C. for 10 minutes and subsequently cooling to 0° C., 50 µl of 2×Boehringer hybridization mix were added and hybridization was carried out at 68° C. for 1 hour. The magnetic beads were pretreated with 1×Boehringer mix and then separated with a magnet from the fluid, which was pipetted off; the beads were then added to the hybridization mixture, which was incubated at room temperature for ½ hour with gentle movement. The coupled hybridization complex was separated with the beads from the residual fluid, which was pipetted off; the beads were washed once with buffer A (2× SSC; 0.1% SDS) and then twice with buffer B (0.1 SSC; 0.1% SDS). The magnetic particles were taken up in 200 µl of SauIIIa restriction enzyme buffer and, after adding 2 units of SauIIIa restriction enzyme, the fluorescence-labelled DNA was cleaved from the beads at 37° C. for 1 hour.

Subsequently, 400 µl of double-distilled water were added and the fluorescence of the DNA was measured in a fluorescence photometer.

Example 20

Liquid hybridization using amplified, fluorescence-labelled target DNA

The liquid hybridizations were carried out as reversed-phase tests. For this purpose, a Nitrosomonas-specific 1.7 kb gene probe was biotinylated at the 3' end using a 3' end-labelling kit from Boehringer and then hybridized as in Example 19 with fluorescence-labelled, amplified genomic DNA from Nitrosomonas. The fluorescent hybridization complex was separated out of the total mixture, by way of the biotinylated gene probe, on streptavidincoated magnetic particles and, after appropriate washing steps, the fluorescent DNA was cleaved from the magnetic particles using SauIIIa restriction enzyme as in Example 19 and measured in a fluorescence photometer.

---

We claim:

1. A fluorescent nucleotide of the formula:

A—B—C in which

A represents a natural or synthetic nucleotide;

B represents a bridging member having two linkable centers; and

C represents a coumarin residue of the formula:

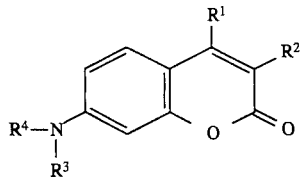

wherein $R^1$ represents hydrogen or cyano;

$R^2$ represents sulphophenyl or sulphothiazolyl, which is bound in the 2, 4 or 5 position and is further unsubstituted or substituted;

$R^3$ represents H, or represents $C_{1-4}$-alkyl or $C_{1-4}$-alkoxycarbonyl-$C_{1-4}$-alkyl, in which $C_{1-4}$-alkyl is unsubstituted or substituted by hydroxyl, amino, carboxyl, $C_{1-4}$-alkoxycarbonyl or sulpho, or represents phenylsulphonyl, which is unsubstituted or substituted once or more than once by chlorine, bromine, $C_{1-4}$-alkyl or sulpho;

$R^2$ or $R^3$ can be substituted by a primary or secondary amino group, hydroxyl, carboxyl or $C_{1-4}$-alkoxycarbonyl or itself represent such a substituent, or $R^2$ or $R^3$ can be converted by hydrolysis into such a group; and $R^4$ represents a substituent or a bond to B and, in the event that $R^4$ represents a substituent, then the bonding of C to B is effected by way of a further substituent on $R^2$.

2. A fluroescent nucleotide according to claim 1, wherein:

A represents a natural or synthetic nucleotide selected from the group consisting of AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-MeO-CMP, 5-MeO-CDP, 5-MeO-CTP, and the corresponding deoxynucleotides or dideoxynucleotides;

B represents a bifunctional linear or branched bridging member having a chain length of up to 50 atoms, where said atoms are selected from the group consisting of C, H, O, N or S;

$R^2$ represents sulphophenyl or sulphothiazolyl, bound in the 2, 4 or 5 position, where sulphophenyl is unsubstituted or substituted by carboxyl, $C_{1-4}$-alkylcarbonyloxy, amino, $—NH—C_{1-4}$-alkyl, $—(CH_2)_{1-4}—NH_2$, $C_{1-4}$—alkyl, cyano, fluorine, chlorine, bromine or sulpho, and where sulphothiazolyl is unsubstituted or substituted, or represents sulphobenzothiazolyl, where the benzo ring is condensed in the 4 and 5 positions of the thiazolyl ring and where the sulphobenzothiazolyl is unsubstituted or substituted;

$R^3$ represents hydrogen, methyl, ethyl, $—(CH_2)_{1-4}—OH$, $—(CH_2)_{1-4}—NH_2$, $—(CH_2)_{1-4}—COOH$ or $—(CH_2)_{1-4}—SO_3H$; and $R^4$ represents a bond.

3. A fluorescent nucleotide according to claim 2, wherein:

B represents a bifunctional linear or branched bridging member having a chain length of 2 to 20 atoms, where said atoms are selected from the group consisting of C, H, O, N or S;

$R^2$ represents sulphophenyl or sulphothiazolyl, bound in the 2, 4 or 5 position, where sulphophenyl is unsubstituted or substituted by paracarboxyl, para-amino, para—NH—$C_{1-4}$-alkyl, para—$CH_2$—$NH_2$, cyano, methyl or ethyl, and where sulphothiazolyl is unsubstituted or substituted by chloro, cyano or carboxyl, or represents sulphobenzothiazolyl, where the benzo ring is condensed in the 4 and 5 positions of the thiazolyl ring and where the sulphobenzothiazolyl is unsubstituted or substituted by carboxyl or amino.

4. A fluorescent nucleotide according to claim 3, wherein:

B represents a bifunctional bridging member selected from the group consisting of peptide, hydrocarbon, polyalcohol, polyalkoxide, polyether, polyamine, polyimine and carbohydrate bifunctional bridging members.

5. A fluorescent nucleotide according to claim 3, wherein:

B represents a bifunctional bridging member selected from the group consisting of alkylene, alkenylene, alkynylene and arylene.

6. A fluorescent nucleotide according to claim 3, wherein:

B represents a bifunctional bridging member selected from the group consisting of —CH=CH—$CH_2$NH—, -glycyl-glycyl-glycyl-, —NH($CH_2$)$_5$CO—, spermine, spermidine, —NH—($CH_2$)$_6$—NH—, —NH—$CH_2CH_2$—NH—, —CH=CH—$CH_2$—NH—CO—($CH_2$)$_5$—NH —CO— and —CH=CH—$CH_2$—NH—CO—($CH_3$)$_5$—NH —CO—($CH_2$)$_3$13.

7. A fluorescent nucleotide of the formula:

A—B—C in which

A represents a natural or synthetic nucleotide selected from the group consisting of AMP, ADP, ATP, GMP, GDP, GTP, CMP, CDP, CTP, UMP, UDP, UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-Me-OCMP, 5-MeO-CDP, 5-MeO-CTP, and the corresponding deoxynucleotides or dideoxynucleotides;

B represents a bifunctional bridging member selected from the group consisting of alkylene, alkenylene, alkynylene, arylene, —CH=CH—$CH_2$NH—, -glycyl-glycyl-glycyl-, —NH($CH_2$)$_5$CO—, spermine, spermidine, —NH—($CH_2$)$_6$—NH—, —NH—$CH_2CH_2$— NH—, —CH=CH—$CH_2$—NH—CO—($CH_2$)$_5$— NH—CO— and —CH=CH—$CH_2$—NH —CO— ($CH_2$)$_5$—NH—CO—($CH_2$)$_3$—; and C represents a coumarin residue of the formula:

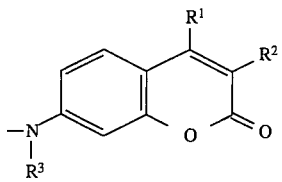

wherein $R^1$ represents hydrogen or cyano;

$R^2$ represents sulphophenyl or sulphothiazolyl, bound in the 2, 4 or 5 position, where sulphophenyl is unsubstituted or substituted by para-carboxyl, para-amino, para—NH—$C_{1-4}$-alkyl, para—$CH_2$—$NH_2$, cyano, methyl or ethyl, and where sulphothiazolyl is unsubstituted or substituted by chloro, cyano or carboxyl, or represents sulphobenzothiazolyl, where the benzo ring is condensed in the 4 and 5 positions of the thiazolyl ring and where the sulphobenzothiazolyl is unsubstituted or substituted by carboxyl or amino;

$R^3$ represents H, or represents $C_{1-4}$-alkyl or $C_{1-4}$-alkoxycarbonyl-$C_{1-4}$-alkyl, in which $C_{1-4}$-alkyl is unsubstituted or substituted by hydroxyl, amino, carboxyl, $C_{1-4}$-alkoxycarbonyl or sulpho, or represents phenylsulphonyl, which is unsubstituted or substituted once or more than once by chlorine, bromine, $C_{1-4}$-alkyl or sulpho.

8. A method which comprises enzymatically incorporating a fluorescent nucleotide according to claim 1 into nucleic acids, the enzyme used consisting of a member selected from the group of DNA polymerases, RNA polymerases, reverse transcriptase or terminal transferase.

9. A method which comprises enzymatically incorporating a fluorescent nucleotide according to claim 7 into nucleic acids, the enzyme used consisting of a member selected from the group of the DNA polymerases, RNA polymerases, reverse transcriptase or terminal transferases.

10. Gene probes containing a fluorescent nucleotide according to claim 7.

11. Reagent for detecting nucleic acids containing a fluorescent nucleotide according to claim 7.

12. Gene probes containing a fluorescent nucleotide according to claim 1.

13. Reagent for detecting nucleic acids containing at least one nucleotice according to claim 1.

* * * * *

UNITED STATES PATENT AND TRADEMARK OFFICE
CERTIFICATE OF CORRECTION

PATENT NO. : 5,547,860
DATED : August 20, 1996
INVENTOR(S) : Kocher, et al.

It is certified that error appears in the above-indentified patent and that said Letters Patent is hereby corrected as shown below:

Col. 23, line 35   Delete " $-(CH_3)_5$ " and substitute -- $-(CH_2)_5$ --, delete " $-(CH_2)_3 13$ " and substitute -- $-(CH_2)_3-$ --

Col. 24, claim 13   After " containing " delete " at least one nucleotice " and substitute -- a fluorescent nucleotide --

Signed and Sealed this

Eighteenth Day of March, 1997

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 16 Nucleotides
        ( B ) TYPE: Nucleic Acid
        ( C ) STRANDEDNESS: Single
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( B ) STRAIN: Nitrosomonas europeae ( x i ) SEQUENCE DESCRIPTION: SEQ ID NO: 1:
                A T C C A G T T G C   T T C A A C        1 6

( 2 ) INFORMATION FOR SEQ ID NO: 2:

( i ) SEQUENCE CHARACTERISTICS:
        ( A ) LENGTH: 15 Nucleotides
        ( B ) TYPE: Nucleic Acid
        ( C ) STRANDEDNESS: Single
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( B ) STRAIN: Nitrosomonas europeae ( x i ) SEQUENCE DESCRIPTION: SEQ ID NO: 2:
                A C T G G C A G G C   A G C A G        1 5

( 2 ) INFORMATION FOR SEQ ID NO: 3:

```
( i ) SEQUENCE CHARACTERISTICS:
        ( A ) LENGTH: 19 Nucleotides
        ( B ) TYPE: Nucleic Acid
        ( C ) STRANDEDNESS: Single
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( B ) STRAIN: Nitrosomonas europeae ( x i ) SEQUENCE DESCRIPTION: SEQ ID NO: 3:
                    CTGCTCGTAG  ACAATGCGT                                    1 9

( 2 ) INFORMATION FOR SEQ ID NO: 4:

( i ) SEQUENCE CHARACTERISTICS:
            ( A ) LENGTH: 18 Nucleotides
            ( B ) TYPE: Nucleic Acid
            ( C ) STRANDEDNESS: Single
            ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
            ( B ) STRAIN: Nitrosomonas europeae ( x i ) SEQUENCE DESCRIPTION: SEQ ID NO: 4:
                    ATCCAGTTGT  GTCTTAAC                                      1 8
```